(12) United States Patent
Kentgens et al.

(10) Patent No.: US 9,945,918 B2
(45) Date of Patent: Apr. 17, 2018

(54) RAPID CYCLE DYNAMIC NUCLEAR POLARIZATION MAGNETIC RESONANCE APPARATUS

(71) Applicant: Stichting Katholieke Universiteit, Nijmegen (NL)

(72) Inventors: Arnold Peter Maria Kentgens, Oosterhout (NL); Petrus Johannes Maria van Bentum, Nijmegen (NL)

(73) Assignee: Stichting Katholieke Universiteit, Nijmegen (NL)

( * ) Notice: Subject to any disclaimer, the term of this patent is extended or adjusted under 35 U.S.C. 154(b) by 938 days.

(21) Appl. No.: 14/368,011

(22) PCT Filed: Dec. 21, 2012

(86) PCT No.: PCT/EP2012/076628
§ 371 (c)(1),
(2) Date: Jun. 23, 2014

(87) PCT Pub. No.: WO2013/092996
PCT Pub. Date: Jun. 27, 2013

(65) Prior Publication Data
US 2015/0008917 A1    Jan. 8, 2015

(30) Foreign Application Priority Data
Dec. 23, 2011  (EP) .................................... 11195534

(51) Int. Cl.
*G01V 3/00* (2006.01)
*G01R 33/48* (2006.01)
(Continued)

(52) U.S. Cl.
CPC ............. *G01R 33/48* (2013.01); *G01N 33/50* (2013.01); *G01R 33/282* (2013.01);
(Continued)

(58) Field of Classification Search
CPC .................................................... G01R 33/282
(Continued)

(56) References Cited

U.S. PATENT DOCUMENTS

| 2005/0122115 A1 | 6/2005 | Maguire et al. |
| 2008/0104966 A1* | 5/2008 | Stautner .................... F25B 9/14 62/6 |

(Continued)

FOREIGN PATENT DOCUMENTS

| EP | 2146215 | 1/2010 |
| WO | 1996/013735 | 10/1995 |

OTHER PUBLICATIONS

Bart et al., "Optimization of Stripline-Based Microfluidic Chips for High-Resolution NMR, Journal of Magnetic Resonance," 201 (2009) 175-185.
Bart et al., "A Microfluidic High-Resolution NMR Flow Probe," J. Am. Chem. Soc. 2009, 131, 5014-5015.
(Continued)

*Primary Examiner* — Louis Arana
(74) *Attorney, Agent, or Firm* — Occhuiuti & Rohlicek LLP

(57) ABSTRACT

A rapid cycle dynamic nuclear polarization (DNP) NMR apparatus comprises (i) a cooling unit configured to cool a sample in a capillary, (b) a DNP polarization unit configured to polarize the sample in the capillary, (c) a stripline-based NMR detector comprising a stripline for NMR analysis of the sample in the capillary, (d) a transport unit configured to guide the capillary from the DNP polarization unit to the stripline of stripline-based NMR detector; and (e) a heating unit configured to heat the sample in the capillary before analysis of the sample by the stripline-based NMR detector. Fast (1D-3D) NMR measurements with high resolution may be obtained.

20 Claims, 4 Drawing Sheets

(51) Int. Cl.
*G01R 33/28* (2006.01)
*G01R 33/62* (2006.01)
*G01N 33/50* (2006.01)
*G01R 33/31* (2006.01)
*G01R 33/30* (2006.01)
*G01R 33/345* (2006.01)
*G01R 33/465* (2006.01)

(52) U.S. Cl.
CPC ........... *G01R 33/307* (2013.01); *G01R 33/31* (2013.01); *G01R 33/62* (2013.01); *G01R 33/302* (2013.01); *G01R 33/3456* (2013.01); *G01R 33/465* (2013.01)

(58) Field of Classification Search
USPC .......................................... 324/318, 322, 300
See application file for complete search history.

(56) References Cited

U.S. PATENT DOCUMENTS

| | | | |
|---|---|---|---|
| 2008/0290869 A1 | 11/2008 | Hutton et al. | |
| 2009/0051361 A1* | 2/2009 | Slade et al. | |
| 2009/0311189 A1* | 12/2009 | Griffin | G01N 24/08 |
| | | | 424/9.3 |
| 2013/0168576 A1* | 7/2013 | Lohman | G01R 33/282 |
| | | | 250/492.1 |
| 2016/0334476 A1* | 11/2016 | Doty | G01R 33/38 |

OTHER PUBLICATIONS

Gardeniers et al., "Microfluidic High-Resolution NMR Chip for Biological Fluids," IEEE, Jun. 21-25, 2009, 642-1645.
Van Bentum et al., "Stripline Probes for Nuclear Magnetic Resonance," Journal of Magnetic Resonance 189 (2007) 104-113.

* cited by examiner

RAPID CYCLE DYNAMIC NUCLEAR POLARIZATION MAGNETIC RESONANCE APPARATUS

CROSS REFERENCE TO RELATED APPLICATION

This application is the national phase under 35 USC 371 of international application no. PCT/EP2012/076628, filed Dec. 21, 2012, which claims the benefit of the priority date of European application no. 11195534.0, filed Dec. 23, 2011. The contents of the aforementioned applications are incorporated herein in their entirety.

FIELD OF THE INVENTION

The invention relates to a rapid cycle dynamic nuclear polarization (DNP) nuclear magnetic resonance (NMR) apparatus as well as to a method for DNP-NMR analysis with a stripline-based NMR detector.

BACKGROUND OF THE INVENTION

Dynamic nuclear polarization (DNP) is used to enhance the nuclear polarization of samples for use in applications such as nuclear magnetic resonance (NMR) analysis including nuclear magnetic resonance imaging (MRI) and analytical high-resolution NMR spectroscopy (MRS). MRI is a diagnostic technique that has become particularly attractive to physicians as it is non-invasive and does not involve exposing the patient under study to potentially harmful radiation such as X-rays. Analytical high resolution NMR spectroscopy is routinely used in the determination of molecular structure.

MRI and NMR spectroscopy lack sensitivity due to the normally very low polarization of the nuclear spins of the materials used. In view of this, the dynamic nuclear polarization technique has been developed to improve the polarization of nuclear spins.

In a typical DNP process, a liquid sample is mixed with a polarising agent and placed in a sample cup which is mounted to a sample holding tube. The sample holding tube is then inserted into the bore of a superconducting magnet located in a cryostat so as to bring the sample to a working volume within the bore, the working volume being located in a microwave cavity defined by a DNP insert. The superconducting magnet generates a magnetic field of suitable strength and homogeneity in the working volume.

The sample is cooled and solidified by exposing it to liquid helium in the bore and then irradiated with microwaves while it is exposed to the magnetic field and in its frozen state. The sample is then lifted out of the liquid helium to a position in which it is still subject to the magnetic field although this may be less homogeneous. Hot solvent is then supplied into the sample holding tube, typically through a dissolution tube or stick or other solvent conveying system, to the working volume so as to dissolve the polarised sample. Alternatively, the sample may be melted. The solution or melt is then rapidly extracted and transferred for subsequent use for analysis in an NMR system.

At present there are two approaches that have become commercially available in the last few years. In a first approach, as also described above, dissolution DNP is applied. In this method, a paramagnetic radical molecule is mixed with the sample, frozen and cooled down to for instance 2 K. Using microwave irradiation for a time up to several hours, the electron spin polarization is transferred to the molecule under study. The sample is then quickly dissolved, heated to room temperature and transferred to the NMR system, where a single or few scan NMR analysis is performed with superior sensitivity. In another approach, Magic Angle Spinning (MAS) solid state DNP, the sample remains in the solid phase, at a temperature of about 90 K. Using high-resolution MAS-NMR, the samples can be studied in situ.

US2008/290869 describes an apparatus for performing in-vitro DNP-NMR measurements on a sample comprising a magnetic field generating apparatus located in a cryostat and surrounding a bore defining respective NMR and DNP working regions. A system for performing DNP on a suitably prepared sample in the DNP working region is also mentioned. A system for performing a NMR process on a sample in the NMR working region is also mentioned. A sample positioning mechanism which can be inserted in the bore to bring a sample in turn into each of the working regions is also mentioned. The magnetic field generating apparatus is structured so that the magnetic field in the DNP working region has a homogeneity or profile suitable for performing DNP on the sample and the magnetic field in the NMR working region has a homogeneity or profile suitable for performing a NMR process on the sample.

Bart et al, Journal of Magnetic Resonance, vol. 201, no. 2, 1 Dec. 2009, pages 175-185, reports on the optimization, fabrication and experimental characterization of a stripline-based microfluidic NMR probe, realized in a silicon substrate. The stripline geometry was modelled in respect of rf-homogeneity, sensitivity and spectral resolution. The fabrication of the chip is described.

US2005/0122115 describes an electromagnetic field sensor or generator employing a radio frequency micro strip transmission channel formed by a low-loss dielectric substrate sandwiched between a non-resonant micro strip conductor. A discontinuity in said micro strip conductor that substantially alters its cross-sectional dimensions causes electrical signals in the micro strip conductor to be inductively coupled to near field electromagnetic radiation in the vicinity of the discontinuity. The discontinuity may be defined by one or more holes, slots, slits or stubs in the micro strip. The sensor/generator may be used in numerous applications, including NMR spectrometry, as a near field scanning device to inspect operating integrated circuits, or to read or write data on magnetic materials.

EP2146215 describes an apparatus having a magnet arrangement for producing magnetic field in a working volume. The magnet arrangement produces a control field with magnetic field gradients of high orders in a direction of an axis in a working volume. A compensation arrangement of magnetic material is positioned in the latter working volume. The magnetic field gradients of high orders range between −90% and −110% of magnetic field gradients of same orders of the control field of the magnet arrangement in the direction of the axis in the latter volume. Also a method for aligning a compensation arrangement made of magnetic material is described.

WO9613735 describes that an NMR probe positions a flow chamber with first and second flow regions in the high field of an NMR apparatus. A second, downstream, flow region is surrounded by an exciter/detector coil which may be of a conventional type for home- or hetero nuclear detection, while an upstream, first region is excited by an antenna to condition or enhance a downstream measurement. The downstream coil is tuned to detect hetero nuclear resonances, while the upstream coil may be tuned for enhancement of the same or a different species. A cavity, in conjunction with the upstream coil, allows populations and transfer coherence excitation between electrons and nuclei.

US20090051361 describes a coolant sub-assembly for use in a DNP apparatus. The sub-assembly comprises a plurality of concentric jackets surrounding an inner bore tube having first and second opposed ends. The jackets are adapted to inhibit heat flow to the inner bore tube, a DNP working region being defined within the inner bore tube where a DNP process will be performed on a sample in the DNP working region. A coolant supply path extends adjacent an outer surface of the inner bore tube at the DNP working region in order to cool said outer surface, whereby a sample holder assembly can be inserted through the first end of the inner bore tube to bring a sample holder into the DNP working region and can be moved through the second end of the inner bore tube. An auxiliary coolant supply path supplies coolant to a sample, located in use in the sample holder at the DNP working region, through at least one aperture in the inner bore tube wall at the DNP working region. One or both ends of the inner bore tube opens into a coolant waste path for conveying coolant away from the inner bore tube, and wherein the coolant, auxiliary coolant, and waste paths are coupled to pumping means in use to cause coolant to pass along the coolant, auxiliary coolant and waste paths.

J. A. Gardeniers et al., Transducers 2009, Denver, Colo., USA, Jun. 21-25, 2009, W2B.001, pages 1642-1645, describes a silicon-based microfluidic chip with an integrated RF stripline for NMR detection, with high spectral resolution (ca. 1 Hz at 600 MHZ proton resonance) and high sensitivity (ca. 1.2 mM) for mass-limited (600 nL) biological samples, with a particular focus on human cerebrospinal fluid samples.

SUMMARY OF THE INVENTION

Problems in the field of NMR are concerned with sensitivity and resolution. Either NMR does not reach the sensitivity needed for biomolecular screening or for quantitative analyses in their low concentrations in for instance body fluids. The dissolution DNP does solve the sensitivity issue for nuclei with a long spin-lattice relaxation time T1, such as $^{13}$C. However, $^1$H NMR is generally not possible and repetitive measurements needed for example to resolve the molecular structure in a 2D-NMR experiment is not possible. The low temperature MAS approach does not have this restriction but achieves a lower enhancement and for example the $^1$H resolution in the solid state may be insufficient to identify low concentration molecules in a mixture of many unknown substances.

Below, some aspects of state of the art dissolution DNP and magic angle spinning DNP and typical values are indicated. Exact values may vary:

| Aspects | Dissolution DNP | DNP-MAS |
|---|---|---|
| Sensitivity gain | 10.000 | 100 |
| Polarization time | 4 hour | 10 sec |
| Microwave source | IMPATT oscillator | Gyrotron |
| Cryogenic system | Polarizer magnet 4K, flow system 2K | Gyrotron magnet 4K low temp MAS 90 K |
| Cryogenic liquids | >10 l liquid He/day | >100 l liquid N$_2$/day |
| nuclei | 13C 15N | 1H 13C 15N |
| Quantitative | partly | partly |
| Resolution | medium-high | medium |
| 2D/3D | no | yes |
| Sample volume | 3 ml | 200 µl |

Hence, it is an aspect of the invention to provide an alternative rapid cycle dynamic nuclear polarization (DNP) NMR apparatus and/or an alternative method for DNP-NMR analysis with a stripline-based NMR detector, which preferably obviate one or more of above-mentioned drawbacks.

With the present invention we propose a new method "Rapid cycle-DNP" which will allow repetitive polarization analysis cycles as well as a new NMR apparatus, indicated as "Rapid cycle-DNP" NMR apparatus that can be used in such method. The proposed new method enables sensitive NMR analysis of low concentration samples in a fraction of the time needed in conventional liquid or solid state NMR. It also is fairly generic in the sense that it puts no special restrictions for the molecules under study.

In a first aspect, the invention provides a rapid cycle dynamic nuclear polarization (DNP) NMR apparatus ("apparatus") comprising:
- a cooling unit, configured to cool a sample in a (flow-through) capillary;
- a DNP polarization unit ("polarization unit") configured to polarize the sample in the capillary;
- a stripline-based NMR detector comprising a stripline for NMR analysis of the sample in the capillary;
- a transport unit configured to guide the capillary from the DNP polarization unit to the stripline of stripline-based NMR detector; and
- a heating unit configured to heat the sample in the capillary before analysis of the sample by the stripline-based NMR detector.

In a further aspect, the invention provides a method for DNP-NMR analysis with a stripline-based NMR detector as defined herein, the method comprising:
i. loading a sample comprising an analyte and a polarizing agent in a (flow-through) capillary, the sample having a volume in the range of 1 nl-20 µl;
ii. guiding the sample in the capillary to the microwave resonator to arrange the sample in the microwave resonator, (preferably) cooling the sample, especially to a temperature below the freezing temperature of the sample (such as below 120 K), and generating microwaves selected from the range of 1-1000 GHz within the microwave resonator to polarize the sample;
iii. guiding the capillary to the stripline of the stripline-based NMR detector to arrange the sample over a stripline, (preferably) thawing the sample (e.g. heating the sample to a temperature of at least 273 K), applying (a magnetic field) and RF pulses to the sample, and retrieving an NMR signal of the sample in the capillary.

Some non-limiting aspects that may apply to the presently proposed apparatus and method are displayed in below table:

| | Rapid cycle-DNP |
|---|---|
| Sensitivity gain | 500 |
| Polarization time | 10-30 sec |
| Microwave source | Diode/Extended Interaction Klystron (EIK) or Gyrotron |
| Cryogenic system | e.g. Low temp polarizer (77 K) |
| Cryogenic liquids | <10 l liquid N$_2$/day |

-continued

| | Rapid cycle-DNP |
|---|---|
| nuclei | 1H 13C 15N |
| Quantitative | Yes |
| Resolution | High |
| 2D/3D | Yes |
| Sample volume | 1 nl-20 µl, especially 5-500 nl |

A further large advantage of the proposed method is that also proton NMR is possible with no compromises with respect to resolution. It allows fast micro fluidic automated sample handling for 1D NMR screening and additional 2D/3D structure elucidation as is common in liquid state NMR. The main advantage could be that in-line proton NMR screening can be combined with natural abundance 13C NMR at lower cost and lower complexity compared with its commercial counterparts.

At present, an enhancement of the NMR signal in the liquid state of ×165 at room temperature has been demonstrated. Similar numbers are published for the 90 K solid state polarization. Experiments show that the enhancement rises steeply for lower temperatures and a reduction to 77 K or below can further improve the enhancement by a factor 2 to 3. The temperature step to room temperature adds a factor 3 compared to room temperature Boltzmann numbers. Many of the practical problems of the dissolution method (sample loss, reduction in resolution due to turbulence etc.) can be avoided.

Potential applications can be found in the field of metabolic screening, in line quality control (impurity levels, composition and concentration). The method does not require additional magnet cryostats and can be built on a much more compact platform.

With prior art solutions, there are often no options for repeated measurement and/or no options for automated liquid sample loading. Often, a special dual center magnet is needed and/or conventional NMR detection (no stripline) is applied. Further, no options for fast in situ melting are available. Hence, no liquid sample loading and/or no shuttling of frozen samples in a continuous capillary is available in the prior art.

The above apparatus and method are further elucidated below, following the process stages as defined in the method of the invention. The sample volume may for instance be in the range of 1 nl-20 µl. As indicated above, a capillary is used. Especially, the capillary comprises an inlet and an outlet. In this way, the capillary can be used as flow-through capillary. Hence, the capillary is herein also indicated as flow-through capillary. The term "capillary", as known in the art, especially relates to a tube with an inlet and an outlet, and in general having a small (internal) diameter. The fact that a (flow-through) capillary is applied does not necessarily imply that the sample has to flow through the entire capillary. Of course, when executing the method of the invention, the sample may also flow through part of the capillary. The apparatus may thus allow a flow of one or more samples through the capillary (when the one or more samples (and one or more buffers) are in the liquid state, and the apparatus may allow transport of the capillary through the apparatus. In this way, there may be two options to transport the sample, which transport options may be used for different stages of the method for measuring the one or more samples. Hence, the capillary may thus be a flow-through capillary. Further, the apparatus may also be a kind of flow-through apparatus, as the capillary may be transported through the apparatus, at least through the DNP stage to the NMR stage (and optionally also back; and optionally also repeatedly back and forth).

The internal diameter of the capillary may for instance be in the range of 0.05-2 mm, such as 0.1-2 mm. The sample at least comprises (a mixture of) an analyte and a polarizing agent. Hence, the method may include loading a sample comprising an analyte and a polarizing agent in a capillary, the sample having a volume in the range of especially 1 nl-20 µl, like 1-10 µl. The capillary may for instance have a length of 0.5-5 m. Especially, the capillary has dimensions that allow bending of the capillary, such as allowing bending with a radius of 1 m or less, such as 0.5 m or less. In this way, the capillary has flexibility which may be beneficial when transporting the capillary (see below). Hence, in a specific embodiment, the capillary is flexible. The flexibility may for instance be due to the dimensions of the capillary and/or the material of which the capillary is made. For instance, the capillary may be bent with a radius of 2 meter or less, such as 1 meter or less, without breaking. Further, in an embodiment the capillary is configured to contain a plurality of samples, separated by buffers (see below). The capillary may for instance be of fused quartz or of polymeric material. During operation of the method of the invention, the capillary may be configured through a large part of the apparatus, such as through the polarization unit and (optional) cooling unit, the (optional) heating unit and the NMR measurement stage. The capillary may be connected to the sample loading unit (see below), and through transport of the sample and through translation of the capillary, the sample may effectively be transported from the sample loading unit to the polarization unit and (optional) cooling unit (by flow of the sample through the capillary) and from the polarization unit and (optional) cooling unit to NMR stage and (optional) heating unit (by translation of the capillary). Hence, the apparatus may be configured to contain a capillary, such as of a length of 0.5-5 m, during the measurement process, wherein the capillary is present in the polarization unit and over the stripline. Hence, during execution of the method, the capillary may be within a significant section of the magnet bore, or even extend beyond on or both sides of the bore.

An advantage of using the capillary in combination with a transport unit is that the probe or sample when in liquid state can be arranged in the capillary (at a predetermined position). Even more, a plurality of probes (samples) may be arranged within the capillary, wherein the probes may be separated by buffer (plugs). By flow and or translation of the capillary, the samples can be arranged in the DNP polarization unit. Then, by translation of the capillary, with the transport unit, the probe(s) can be arranged over the stripline. Multiple measurements can be done by shuttling between the DNP polarization unit and the NMR measurement stage (i.e. over the stripline).

In a specific embodiment, wherein the probe is maintained in a liquid state (thus not cooled to a temperature at or below the freezing point), the transport between the stages in the NMR apparatus is executed by flow of the sample through the capillary. Hence, in such embodiment, the NMR apparatus may further include a sample transporter, that is configured to transport the (liquid) sample through the capillary. For instance, this sample transporter may include a pump. Alternatively or addition, both sample transport options may be applied together.

The transport unit (or actuator) can thus be used to shuttle the sample back and forth, such as between the DNP stage (including optional cooling (stage)) and NMR stage. The distance to be bridged may be within a few centimeters, such as 1-5 cm.

The analyte is a species, such as a liquid, that is to be investigated. Especially, the analyte comprises analyte molecules, i.e. molecules in the analyte to be investigated. Especially, the analyte comprises a liquid, such as a body fluid (liquid). In an embodiment, the analyte comprises a liquid comprising a metabolite (example of analyte molecule). Especially, the analyte comprises a body fluid such as selected from the group consisting of blood, blood plasma, urine, cerebro spinal fluid (Cerebrospinal fluid (CSF), Liquor cerebrospinalis). The polarizing agent makes it possible to transfer the large Boltzmann polarization of the electron spin reservoir (of the polarizing agent) to the nuclear spin reservoir (of one or more analyte molecules) to provide a boost in NMR signal intensities by several orders of magnitude; thus increasing the signal intensity and data acquisition rate in a NMR experiment dramatically. This is the principle of Dynamic Nuclear Polarization (DNP). The polarizing agent may for instance comprise one or more of a free radical molecule, or an immobilized radical molecule containing one or more unpaired electron spins or photo-excited triplet spins. Examples are for instance molecules like TEMPO (2,2,6,6-tetramethylpiperidin-1-oxyl) or trytil (tris (8-carboxy-2,2,6,6-tetramethyl(-d3)-benzo[1,2d:4,5-d'] bis(1,3)dithiol-4-yl) methyl). Optionally a combination of polarizing agents may be applied.

The sample, i.e. the combination of at least the analyte and the polarizing agent are in general liquid at room temperature (RT). In case the combination of analyte and polarizing agent would not be liquid at RT, one or more suitable solvents may be chosen to provide a liquid sample. Note that the sample under investigation does not necessarily comprise the analyte. The phrase "sample comprising an analyte" may thus also be understood as sample that may comprise such analyte". Such sample can be investigated on the presence of such analyte and/or on the behaviour of such analyte (when actually present).

One sample may be loaded to the capillary, however, also a plurality of samples may be loaded to (i.e. introduced in) the capillary. Hence, the term "sample" may also refer to a plurality of (different) samples. The term "different" may relate to different analytes and/or different polarizing agents and/or different ratios of the analyte and polarizing agent, etc. The plurality of samples may be interspaced by buffer volumes ("plugs"), such as buffer liquids. A suitable buffer liquid may for instance be fluorinert (perfluorohexane ($C_6F_{14}$) or perfluoro(2-butyl-tetrahydrofurane)).

For loading the sample to the capillary, a sample loading unit may be applied. Hence, the rapid cycle dynamic nuclear polarization apparatus may further comprise a sample loading unit, which may especially be configured to provide the sample comprising an analyte and a polarizing agent (e.g. DNP radical(s)) and introduce the sample (including e.g. the DNP radical) to the capillary. Further, such sample loading unit may further also be configured to load to the capillary one or more buffer volumes or plugs to separate individual samples. Hence, in an embodiment, the sample loading unit may be configured to load a plurality of samples and a plurality of buffer plugs to the capillary, with adjacent samples being interspaced by buffer plugs. Note that each sample may be different. Hence, the sample loading unit may also be configured to load different samples to the capillary. The sample loading unit may in an embodiment comprise one or more mixing chambers and one or more inlets, especially configured to allow introduction into the sample loading unit of one or more analytes, one or more polarizing agents, one or more buffer liquids, and optionally one or more other species, such as one or more solvents. Note that the sample loading unit may also be configured to allow introduction of a sample (already) comprising the analyte and the polarizing agent. However, the sample loading unit may also be configured to mix an analyte and a polarizing agent and optionally one or more further species such as one or more solvents, such as a supercritical solvent (see also below). The sample loading unit may also be configured to mix a sample (comprising the analyte) and a polarizing agent and optionally one or more further species such as one or more solvents, such as a supercritical solvent (see also below).

In an optional embodiment, the capillary can be connected in line to a chromatography instrument. The sample can then be separated into several sections containing different molecules or mixtures of molecules. Using, buffer plugs these sections will remain separated and do not mix. Alternatively, one can choose to select a specific volume from the chromatography output for further DNP/NMR analysis. For polarization in the solid phase, there is in general no particular restriction to the solvent. For polarization in the liquid state it can be advantageous to use non-protonated solvents with a low viscosity such as super-critical $CO_2$ as the carrier liquid. The absence of dielectric losses in this medium allows the use of much larger volumes without serious heating problems and/or deterioration of the Q-factor of the resonator. More specifically, the use of supercritical solvents may allow efficient liquid state DNP at magnetic fields in the range of 5-20 T, commensurable with the present state of the art in NMR instrumentation. The capillary configuration is especially compatible with high pressure applications, with substantially no loss of sensitivity for the NMR detection and without serious safety issues.

After loading the sample(s) to the capillary, the sample in the capillary is guided to the polarization unit to arrange the sample in the microwave resonator. This may be achieved by a transport of the capillary (itself), but may especially be achieved by transport of the sample within the capillary. As the sample (and the buffer) is liquid when loading to the capillary, the sample (and buffer) may also be transported within the capillary. Hence, when loading the sample to the capillary, part of the capillary may be arranged within the resonator. Hence, during processing, the capillary may (still) be connected to the sample loading unit and may partly be configured within the polarization unit (especially its microwave resonator or microwave cavity). For transport of the sample within the capillary, the sample loading unit may (further) be configured to transport the sample within the capillary. For instance, by controlling the (liquid) pressure on the sample within the capillary, the sample may be transported through the capillary.

The apparatus may further comprise a cooling unit, configured to cool the sample in a capillary. Especially, this cooling is performed when the sample is within the polarization unit. Hence, the cooling unit may especially be configured to cool (during execution of the method) the capillary with sample within the polarization unit. The cooling unit may be configured to cool the sample, especially to a temperature below the freezing point of the sample. The sample is preferably entirely frozen before further processing. However, cooling is optional, see also below. Further, the cooling may be configured to cool the sample either in a controlled way or rapidly ("flash freezing"). In this way, an amorphous frozen state of the sample may be achieved. In an embodiment, the cooling unit is configured to cool the sample to a temperature of 120 K or lower. In a specific embodiment, the cooling unit is liquid $N_2$ based, and may be configured to cool the sample, especially to a temperature selected from the range of 77-100 K. In yet another embodiment, the cooling unit is liquid He based, and may be configured to cool the sample, especially to a temperature selected from the range of 4.2-77 K, especially 4.2-20 K, or even lower. Therefore, in an embodiment the cooling unit is a $N_2$ or He based cooling unit. Hence, especially the method may include cooling the sample in the polarization unit (especially within the microwave resonator) to a temperature below 20 K. The cooling unit may be configured to cool the sample by flowing a cold gas, such as the vapour of boiling $N_2$, or the vapour of boiling He, along the capillary with sample (within the polarization unit). Hence, in a specific embodiment, the cooling unit may comprise a blower for a cold gas. The cooling unit may especially be designed to flash freeze (or blast freeze) the sample. Likewise, the method may (thus) include flash freezing the sample. If desired, also temperatures below 4.2 K may be applied. In another embodiment, a (cooling) mantle may be applied within the polarization unit. Cooling liquid may be provided inside the mantle. The cooling unit may—in an embodiment—comprise a pump for the circulation of the cooling liquid to the polarization unit, such as the above mentioned mantle. Especially, transport of the sample to the cooling unit (or cooling stage) is done by transport of the capillary (with the transport unit or actuator), as this may especially be quick enough toe freeze the sample in an amorphous state.

Further, the sample may now be subjected to microwaves of the polarization unit. To this end, the NMR apparatus further comprises a DNP polarization unit configured to polarize the sample in the capillary. The polarization unit may especially be configured to polarize the sample by generating microwaves selected from the range of 1-1000 GHz, especially 95-560 GHz. Hence, the method of the invention further includes (after loading the sample in a capillary) guiding the sample in the capillary to the polarization unit to arrange the sample in the polarization unit, cooling the sample to a temperature below the freezing temperature (of the sample), such as especially to a temperature of 120 K and lower, and generating microwaves selected from the range of 1-1000 GHz within the polarization unit to polarize the sample. Good polarization may take place within a few minutes. In a specific embodiment, the method comprises polarizing the sample in a time frame in the range of 1-100 sec., or 1-10 sec.

The position where the sample is subjected to microwave radiation is indicated as microwave resonator or microwave cavity (or polarization stage). This is (especially) situated within the bore of a, in general superconducting, magnet. The superconducting magnet generates a magnetic field of suitable strength and homogeneity in the working volume of the microwave resonator. Hence, the stage of subjecting the sample to microwave radiation, i.e. polarizing the sample, is performed in the presence of a magnetic field of the magnet. This is the same magnetic field as applied (in a later stage) for generating the NMR signal. The (static) magnetic field $B_0$ of the magnet within the bore is in general at least 3 Tesla, preferably at least 7 Tesla, such as at least 14 Tesla. In an embodiment, the (static) magnetic field $B_0$ of the magnet within the bore is in general up to 35 Tesla, like up to 25 Tesla, such as up to 20 Tesla, like up to 15 Tesla.

After the polarization, the sample can be transported to the NMR detector, which is especially a stripline based NMR detector. In an embodiment, the stripline is integrated in a micro chip. Stripline based NMR detectors are known in the art, and are for instance described in the following publications, which are herein incorporated by reference, P. J. M. van Bentum, J. W. G. Janssen, A. P. M. Kentgens, J. Bart, J. G. E. Gardeniers, "Stripline probes for NMR," J. Magn. Reson., vol. 189, pp. 104-113, 2007; J. Bart, A. J. Kolkman, A. J. Oosthoek-de Vries, K. Koch, P. J. Nieuwland, J. W. G. Janssen, P. J. M. van Bentum, K. A. M. Ampt, F. P. J. T. Rutjes, S. S. Wijmenga, J. G. E. Gardeniers, A. P. M. Kentgens, "A Microfluidic high-resolution NMR flow probe," J. Am. Chem. Soc., vol. 131, pp. 5014-5015, 2009; and J. Bart, J. W. G. Janssen, P. J. M. van Bentum, A. P. M. Kentgens, J. G. E. Gardeniers, "Optimization of stripline-based micro fluidic chips for high-resolution NMR", J. Magn. Reson., vol. 201, pp. 175-185, 2009. In contrast to helical coils, the stripline has some properties that make the susceptibility problem much easier to handle. The first aspect is that the axis of the stripline is (especially) oriented parallel to the static field $B_0$. The magnetization of the copper strip (i.e. the stripline) is homogeneous and oriented parallel to the external field. From Maxwell's equations it can be derived that for an infinitely long strip there is no field inhomogeneity at the position of the sample, and therefore the ultimate resolution provided by the magnet should be attainable. Because of the constriction shape, the infinite long strip shape is slightly disrupted, which can optionally be compensated by adding a susceptibility matched proton free fluoropolymer at the places where the copper is removed. The stripline configuration represents a simple and effective design for mass-limited NMR samples that is easy to produce with micromachining methods. Attractive points are the fact that the sensitivity can be competitive with optimized helical coils and many of the problems encountered in planar helices are absent. In essence, the high sensitivity and high $B_1$-field of the helical micro coils is conserved. The simple planar design allows a quantitative modeling of both static and high frequency components using analytical or 2D and 3D finite element analysis. A strong advantage of the present design is its scalability.

The stripline preferably has a width which is in the order of the internal diameter of the capillary. The stripline may have a length of about 0.1-10 mm, such as 0.5-5 mm. Especially, the stripline-based NMR detector may be configured to analyze a sample volume (within the capillary) in the range of 1 nl-20 µl, such as 5 nl-5 µl. The stripline-based NMR detector may especially be configured to generate RF pulses with frequencies selected from the range of 5-1200 MHz, such as 144 to 850 MHz.

As the sample at the DNP stage is preferably frozen and can be liquid or solid at the NMR stage, the method of the invention further includes guiding the capillary to the stripline of the stripline-based NMR detector to arrange the sample over a stripline, thawing the sample (heating the sample to a temperature of at least 273 K), applying (a magnetic field) and RF pulses to the sample, and retrieving an NMR signal of the sample in the capillary. Hence, within the magnet bore, the capillary is now transported (by the transport unit or actuator) to arrange the sample over the stripline. Further, the sample is quickly thawed and subjected to NMR measurements.

To this end the apparatus further comprises a transport unit and (optionally) a heating unit. The transport unit is especially configured to guide the capillary from the DNP polarization unit to the stripline of stripline-based NMR detector. Hence, in this stage the sample is transported by transporting the capillary. In this way, the sample is transported from the microwave resonator to the stripline within the magnet bore. The sample, within the capillary, is arranged over the stripline. The sample is in general arranged at a distance within the range of 0-5 mm, especially within the range of 0-0.2 mm (distance wall capillary to stripline). Preferably, the distance is below 500 µm, such as below 100 µm. The transport of the capillary from the polarization stage is in general performed at a relative high speed and thus consumes only a short time. Especially, the method may include guiding the capillary (after the polarization stage) to the stripline of the stripline-based NMR detector in a time frame in the range of 10 ms-5 sec. (see also below), such as within less than 0.5 sec. For transport of the capillary, in principle any system ("transport unit") can be used that is able to transport the capillary from the polarization stage to the NMR detection stage. For instance, the transport unit may comprise a rotator configured to transport the capillary, or a linear translator configured to transport the capillary or a piezo transducer to transport the capillary. Combinations of two or more of such elements may also be applied. As can be derived from above, the (apparatus and) transport unit are especially configured to transport the capillary with the sample from the polarization unit to the stripline in a time frame in the range of 20 ms-1 sec.

The heating unit is especially configured to heat the sample in the capillary before analysis of the sample by the stripline-based NMR detector. The sample may be heated during transport of the capillary to the stripline and/or when the sample is arranged over the stripline. Preferably, the time for transport and (optional) heating is in the range of 20 ms-5 sec., such as 20 ms-1 sec. (see also above). In a specific embodiment, the heating unit may comprise a means to bring the capillary with sample in contact with a hot gas flow, such as a blower for a hot gas. Optionally, the heating unit may comprise a means to bring the capillary with sample in contact with a hot liquid. For instance, the capillary may be transported through a bath with hot liquid. Optionally the heating unit may contain a suitable optical heater such as a diode laser that dissipates the energy of the light in the sample volume.

Optionally, the heating unit may also be an RF heater using a separate channel from the NMR apparatus. In NMR it is common to use an LC resonating circuit with the sample in the inductive part to create a magnetic interaction at the proper frequency. In the heater unit one can choose to position the capillary sample in the capacitive section of the LC circuit (also known as "resonant circuit", or "tank circuit", or "tuned circuit"). The large RF electrical field will then lead to rapid sample heating using the dielectric (non-resonant) absorption in the solvent. Hence, in an embodiment the heater is a heater configured to use a separate channel from the NMR apparatus for RF heating a sample (in the capillary).

Alternatively it is also possible to use off-resonant RF excitation in the NMR detector. If the excitation frequency is sufficiently far from the NMR resonances in the sample, dielectric heating occurs without touching the nuclear spin states. A particular advantage of RF heating is the fact that no additional equipment is needed, since the required high power pulsed RF is already available in the NMR apparatus. Hence, in an embodiment, the heating unit may not be a separate unit. As indicated above, the apparatus can be arranged to allow heating of the sample by off-resonant RF excitation in the NMR detector.

The heating stage may be used to heat the sample, especially to thaw the sample (in case the sample was frozen (upstream of the stripline with the optional cooling unit)). Especially, heating may include heating of the sample to a temperature of at least 273 K, especially to a temperature of at least 290 K (within the before-mentioned time frame). In an embodiment, heating includes heating the sample to a temperature where the sample is liquid. Hence, as can be derived from above, the (apparatus and) transport unit and heating unit are especially configured to transport the capillary with the sample from the polarization unit to the stripline and to (optionally) heat the sample until it is non-frozen in a time frame in the range of 20 ms-5 sec, such as in the range of 20 ms-1 sec.

Once the sample has been sufficiently heated (if necessary) and transported to a position over the stripline, the NMR analysis stage has been reached, and the method further involves applying RF pulses to the sample and retrieving an NMR signal of the sample in the capillary. The RF pulses are applied while the sample is within the magnet bore, and is thus still subjected to the stationary magnetic field of the magnet (i.e. $B_0$). In an embodiment, the RF pulses are coupled to the stripline using a quarter lambda coaxial resonator or equivalent LC circuit (sometimes also indicated as resonant circuit or tuned circuit). Hence, the apparatus, especially the stripline-based NMR detector, may (thus) further comprise a quarter lambda coaxial resonator or equivalent LC circuit. The stripline, in combination with the rest of the stripline based NMR detector is also used to detect the NMR signal of the sample. The method may include retrieving an NMR signal from the sample in a time frame in the range of 0.1-10 sec, such as 0.5-2 sec. Hence, within a few minutes, or even quicker, the sample may be (optionally cooled, such as optionally) frozen, polarized (at low temperature), (see also above, (optionally heated, such as optionally) defrozen, and measured.

When the sample is defrozen, the sample may be transported further through the capillary and be removed. However, if desired the sample may also be subject to another cycle. The capillary is returned to a position such that the sample is configured within the DNP polarization unit for a next cooling and polarization stage. Hence, the method of the invention may include repeating method elements ii) and iii). In this way, in a very short time frame the sample may be subject to a number of (different) NMR measurements. For instance, the present method—in contrast to state of the art dissolution DNP NMR—also allows multi-dimensional NMR (on the same sample). Multi dimensional NMR is basically a series of normal 1D NMR experiments with a systematic increment of one of the time constants in the pulse sequence. This allows for example to determine the interaction between neighbouring spins and thus the distance in the molecule or in the crystal. Thus, the only requirement is that the same sample can be studied by NMR in a repetitive way with nearly identical starting situations. This can be achieved in the present method, but not in the case of dissolution DNP. Further, the method of the invention may include an NMR cross-polarization pulse sequence in the NMR stripline to transfer proton polarization to other low gamma nuclei, such as N or C, wherein the sample is still in the frozen state.

Hence, the invention also provides in a further aspect the use of the rapid cycle dynamic nuclear polarization NMR apparatus as defined herein for instance multi-dimensional solid state NMR. The rapid cycle dynamic nuclear polarization as defined herein may for instance be used for metabolic screening or in line quality control (of for instance production lines in the pharmaceutical industry or other chemical synthesis processes).

As indicated above, during the polarization stage, the sample is preferably frozen. However, the sample may also be moderately cooled or not cooled at all and may remain in the liquid stage. In such instance, the Overhauser effect DNP may be applied in either normal or supercritical solvents (under supercritical conditions). Further, in case the sample is solid at the polarization stage, the sample is not necessarily heated to obtain a liquid, as optionally also DNP NMR in the solid state may be performed. Hence, in a further aspect, the invention provides a rapid cycle dynamic nuclear polarization (DNP) NMR apparatus ("apparatus") comprising:

an optional cooling unit, configured to (optionally) cool a sample in a capillary;
a DNP polarization unit ("polarization unit") configured to polarize the sample in the capillary;
a stripline-based NMR detector comprising a stripline for NMR analysis of the sample in the capillary;
a transport unit configured to guide the capillary from the DNP polarization unit to the stripline of stripline-based NMR detector; and
an optional heating unit configured to (optionally) heat the sample in the capillary before analysis of the sample by the stripline-based NMR detector.

In yet a further aspect, the invention provides a method for DNP-NMR analysis with a stripline-based NMR detector as defined in any one of the preceding claims, the method comprising:
i. loading a sample comprising an analyte and a polarizing agent in a capillary, the sample having a volume in the range of 1 nl-20 µl;
ii. (a) guiding the sample in the capillary to the microwave resonator to arrange the sample in the microwave resonator, (b) optionally cooling the sample, such as optionally cooling the sample to a temperature below the freezing temperature of the sample (such as below 120 K), and (c) generating microwaves selected from the range of 1-1000 GHz within the microwave resonator to polarize the sample;
iii. (d) guiding the capillary to the stripline of the stripline-based NMR detector to arrange the sample over a stripline, (e) optionally heating the sample, such as in an embodiment thawing the sample (e.g. heating the sample to a temperature of at least 273 K), (f) applying (a magnetic field) and RF pulses to the sample, and (g) retrieving an NMR signal of the sample in the capillary.

The samples that are measured, or more especially the analytes that are measured, may be in or may be mixed with a (measuring liquid). For instance, in an embodiment a supercritical solvent may be applied. A supercritical solvent is a solvent that can be brought in a supercritical state. Examples of such solvents are e.g. $CO_2$ but also $H_2O$, $N_2O$, $NH_3$, methanol or Freon 22, or mixtures of two or more thereof. Hence, in the present invention, the analyte is measured in the liquid state, while being (solved or mixed) in a supercritical solvent. Hence, the analyte may be solved in such solvent. In another embodiment, the liquid sample comprising the analyte is combined with such solved, to provide a sample with an analyte in a supercritical solvent. Hence, the sample may comprise a supercritical solvent. With a supercritical solvent, H-NMR may be performed with a reduced proton background. Further, also liquid state DNP at high field may be performed when using a supercritical solvent.

The term "substantially" herein, or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The apparatus herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device or apparatus claims enumerating several means, several of these means may be embodied by one and the same item of hardware. The mere fact that certain measures are recited in mutually different dependent claims does not indicate that a combination of these measures cannot be used to advantage.

The invention further applies to an apparatus comprising one or more of the characterising features described in the description and/or shown in the attached drawings. The invention further pertains to a method or process comprising one or more of the characterising features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

The figures are not necessarily on scale.

DESCRIPTION OF PREFERRED EMBODIMENTS

Figure 1A:
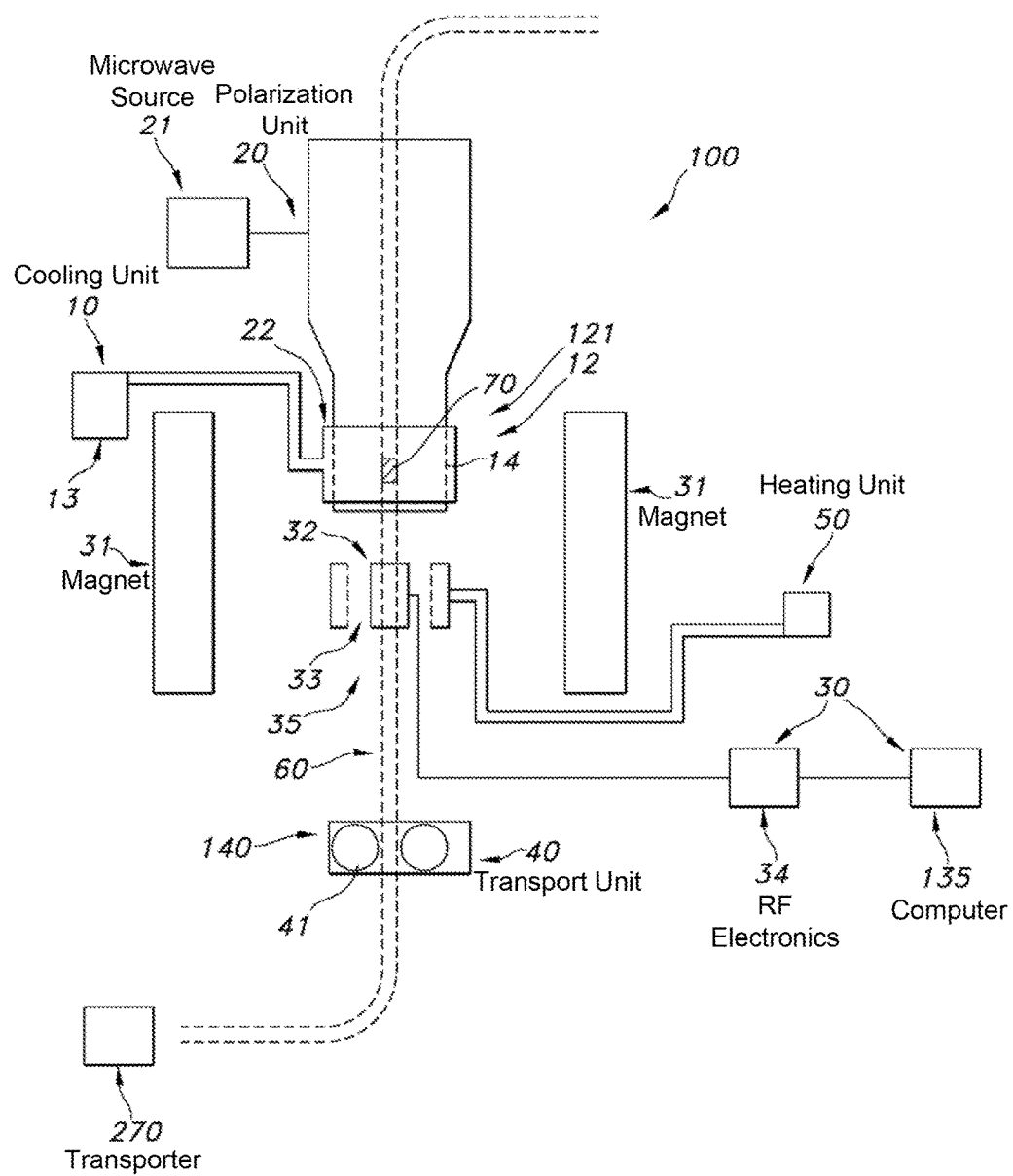
FIGS. 1a-1e schematically depict embodiments and specific features of the apparatus and method as described herein.

FIG. 1a schematically depicts an embodiment of the rapid cycle dynamic nuclear polarization (DNP) NMR apparatus 100 of the invention. The apparatus further comprises a DNP polarization unit 20, especially configured to polarize the sample 70 in the capillary 60. By way of example, the sample is depicted to be in the polarization stage. The polarization unit 20 further comprises a microwave source 21, such as a diode (EIK). The polarization unit 20 further comprises a resonator 22, which is configured within a magnet bore 35 of a magnet 31, of for instance 3.4 Tesla. When the sample is in the resonator 22, the sample is optionally also cooled.

The apparatus therefore comprises a cooling unit 10, configured to cool a sample 70 in a capillary 60. In this embodiment, the cooling unit 10 comprises a reservoir 13 for containing a low-temperature boiling liquid, such as $N_2$ or He. The resonator 22 may comprise a wall or mantle 121 with one or more openings or inlets 14, through which cooling gas may enter the polarization unit 20, especially the resonator 22. In this way, the sample can quickly be cooled to a frozen sample. This is also indicated as cooling stage 12. Cooling is preferred but optional, as one may also apply the DNP Overhauser effect. Hence, even when the cooling unit 10 is present, it may not (always) be applied. Therefore, the cooling unit is preferred, but optional.

The apparatus further comprises a stripline-based NMR detector 30 comprising a stripline 32 for NMR analysis of the sample 70 in the capillary 60. The NMR detector 30 may further comprise RF electronic 34 to control the AC RF pulses through the stripline, and a computer 135.

The apparatus 100 also comprises a transport unit 40 configured to guide the capillary 60 from the DNP polarization unit 20 to the stripline 32 of the stripline-based NMR detector 30. In this schematic embodiment, the transport unit 40 comprises one or more rotatable wheels 41, which can be used to transport the capillary from a position with the sample within the DNP polarization unit to a position with the sample in the NMR stage. The transport unit 40 is also indicated as transport device 140. These may be applied in the translation stage (i.e. the capillary is translated from a first to a second position or stage, and optionally vice versa). Hence, the apparatus may comprise a transport unit or actuator for transport of the capillary 60.

The elements inside the magnet bore are generally mounted in a so-called "probe head". Hence, in general a probe head will be applied. This is indicated with reference 33 (see further FIGS. 1d-1e). During execution of the process, the capillary may thus be configured through the entire probe head.

Further, the apparatus 100 comprises a heating unit 50 configured to heat the sample 70 in the capillary 60 before analysis of the sample 70 by the stripline-based NMR detector 30. The heating unit 50 may be configured to provide a hot gas at the NMR stage (i.e. at to the capillary with sample close to or over the stripline 32). Heating is preferred, but optional, as one may also measure in the solid state. Hence, even when the heating unit 50 is present, it may not (always) be applied. Therefore, the heating unit is preferred, but optional.

Reference 270 indicates a sample transporter configured to transport the sample(s) within the capillary when these samples are in the liquid state. For instance, this can be a pump. Also the sample loading unit, see below, can be used as sample transporter.

Figure 1B:
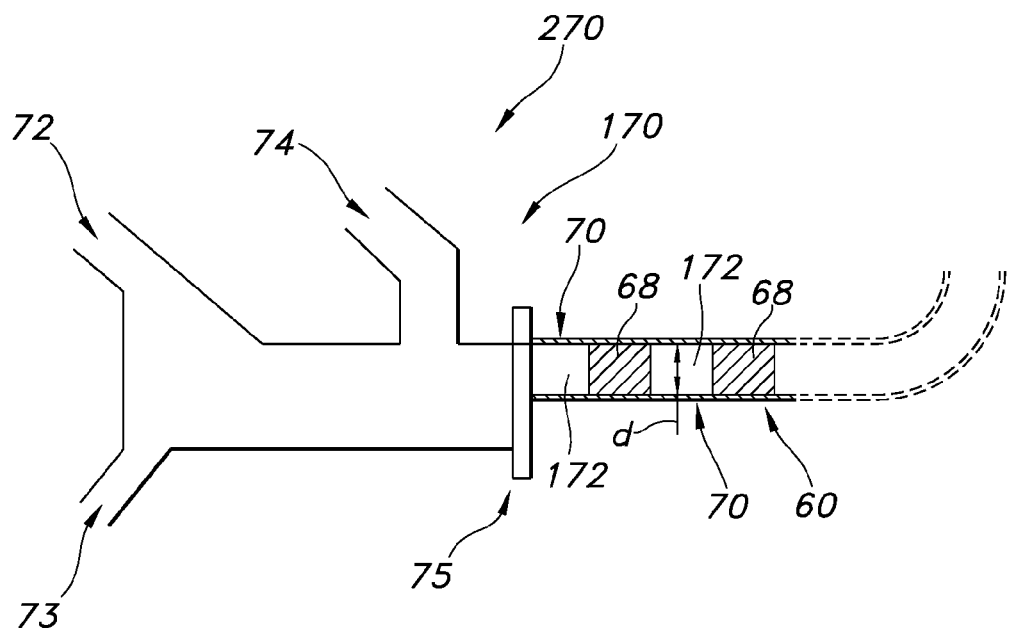

FIG. 1b schematically depicts an embodiment of a sample loading unit 170. As applies also to any of the other schematically embodiments, other configurations may also be possible. The sample loading unit is depicted with a capillary 60 attached. The capillary is loaded with alternating samples 70 (in the form of sample plugs 172) and buffer or buffer plugs 68. The internal diameter of the capillary 60 is indicated with reference d. If desired, a valve may be present, to (partly) allow or (partly) prevent transport of liquid to the capillary or back into the sample loading unit 170. The sample loading unit 170 further comprises inlets 72,73,74, which may for instance be used for introduction of analyte, polarizing agent and buffer, respectively, although optionally further species like one or more solvents may also be introduced in the sample loading unit. As indicated above, the sample loading unit can be used as sample transporter 270; though optionally a separate sample transporter may be applied.

Figure 1C:
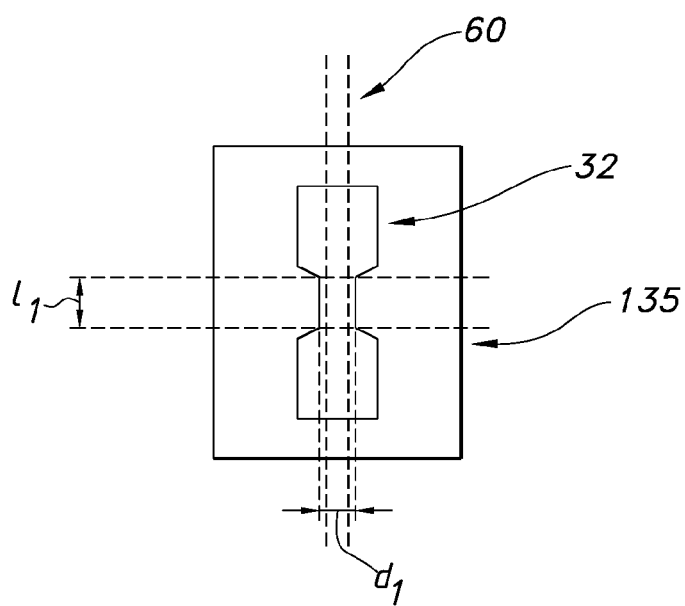

FIG. 1c schematically depicts the stripline 32. It is a narrow electrically flat conductive part having for instance a length 11 of about 0.1-10 mm, such as 0.5-5 mm, and a width d1 of about 0.1-1 mm. By way of example, a capillary is configured over the stripline. Preferably, the stripline has a width, comparable to the capillary inner diameter. Hence, the capillary used especially has an internal diameter in the range of 0.1-1 mm.

Figure 1D:
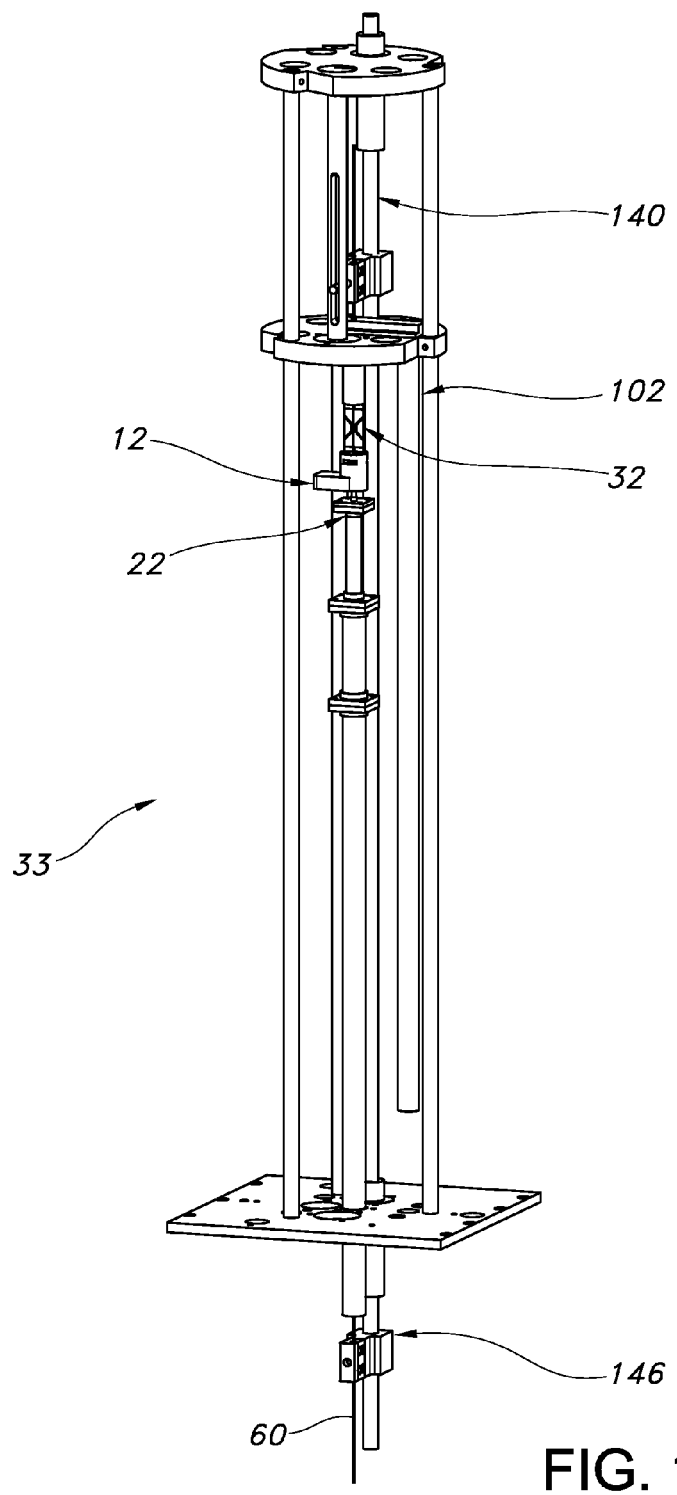
Figure 1E:
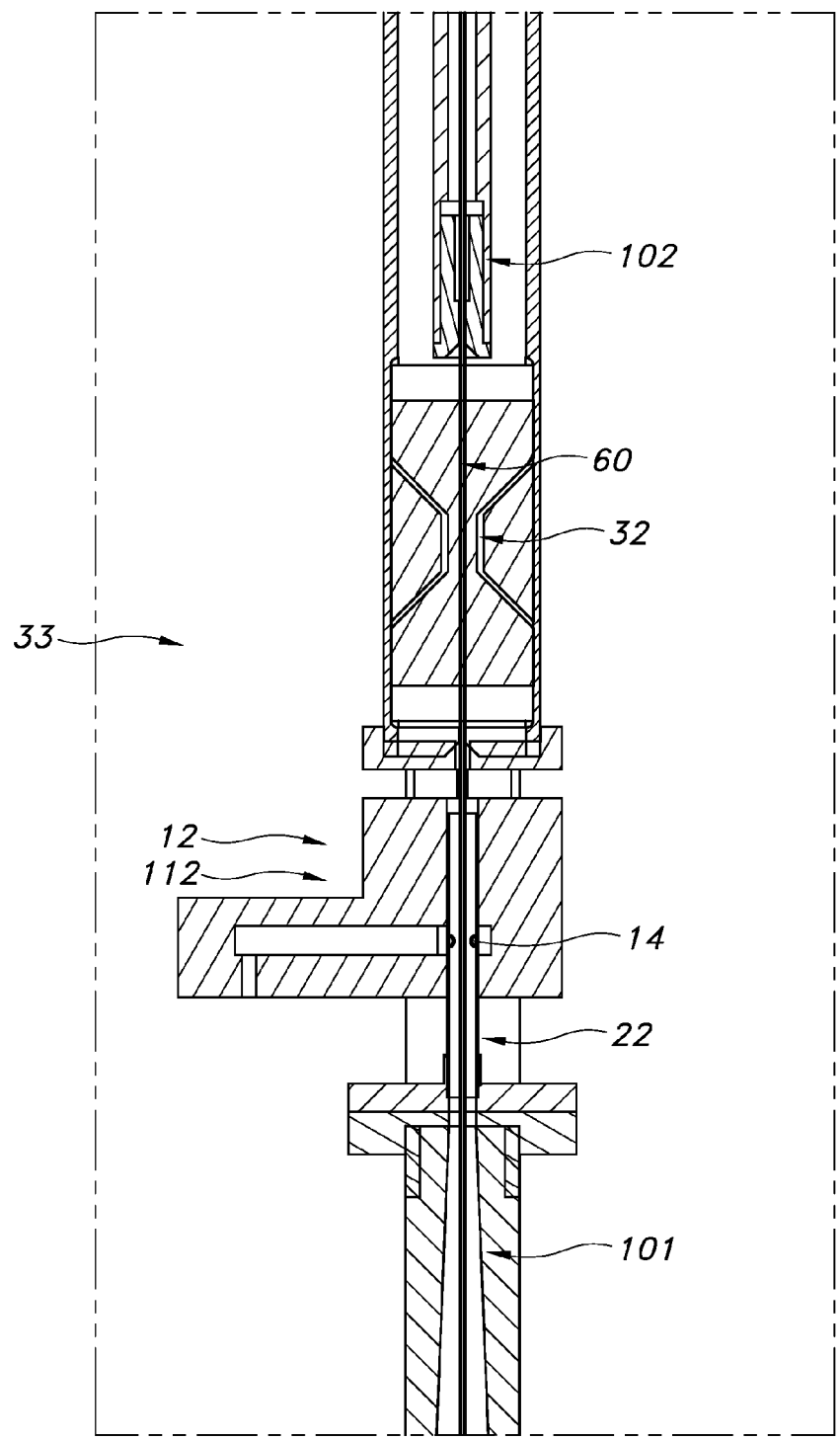

FIG. 1d-1e schematically depicts an embodiment of the probe head 33. The probe head may be arranged in its entirety in the magnet bore 35 of the magnet. During operation, part of the capillary 60 is within probe head 33 and also transported through the probe head 33 (when guiding the capillary from the polarization stage to the NMR detection stage). By way of example, the capillary is depicted. Reference 102 indicates the connection to the NMR (lambda/4) resonator. The stripline 32 is (in this embodiment) part of the probe head 33. Further, the cooling stage is indicated with reference 12; a cooling block with reference 112, the resonator with reference 22. Reference 14 indicates inlets or opening within a mantle or wall 121 of introduction of cold gas in the space where the capillary with sample is arranged. Reference 101 indicates a waveguide taper. References 140 indicate translation device(s). FIG. 1e schematically depicts part of the bore head 33 enlarged.

As can be derived from above, in an embodiment the capillary comprises an inlet and an outlet, said capillary running through said apparatus. Thus it may provide a continuous capillary for transporting a sample through the apparatus. Further, in an embodiment, the optional cooling unit may be elongated. It can comprise a passage for passing the capillary through the cooling unit. In an embodiment, the passage is surrounded by cooling surfaces for cooling the sample in the capillary. Further, in an embodiment, the polarization unit encloses the capillary. It may comprise a passage for the capillary. The cooling unit may at least partially surround the polarization unit. The stripline may thus be configured downstream of the polarization unit (within the probe head). The heating unit may be positioned downstream of the polarization unit and the optional cooling unit. In an embodiment, it at least partially surrounds the stripline. In an embodiment, the heating unit has a passage for the capillary. In an embodiment, the stripline is positioned inside the passage of the heating unit. The sample loading unit may be configured upstream of the polarization unit; the polarization unit may be configured upstream of the stripline and optional heating unit. The optional cooling unit may be configured upstream of the stripline and optional heating unit. The terms "upstream" and "downstream" especially relate to the transport direction of the sample, which may be transported through the capillary from the sample loading unit in a direction of another end of the capillary.

The NMR measurement procedure can be fully automated using the following sequence:
1) sample loading (syringe pump, HPLC robot), mixing with radical and possible additives as a small plug in a Fluorinert host into a small diameter capillary. Sample volumes can be for instance selected in the 10 nl to 10

μl range. A series of several tens to hundreds samples can be sequenced in a pipeline.
2) micro fluidic transport in the capillary to the microwave cavity. At this point the micro fluidic pumps are stopped and switches (for instance valve 75) ensure a fixed position of the sample in the capillary.
3) (Nitrogen) cooling is switched on. This flow will remain on during the remainder of the experiment.
4) Fast injection of the first sample in the pipeline actuator (see also 6) may ensure an amorphous frozen state.
5) the microwave source is switched on to polarize the first sample (for instance 1-30 sec)
6) using a linear actuator or a stepper motor pulley (embodiments of the transport unit), the sample will be transported in the frozen state along with the capillary to the NMR stripline coil. The transport time (for instance 10-500 ms) will be much shorter than the nuclear relaxation time at this temperature.
7) At the heater section, the optionally frozen sample will be optionally melted and heated fast to a chosen temperature in the liquid state. The heater may optionally be integrated in the NMR detector.
8) At the NMR detector (stripline), a temperature regulated ($N_2$) gas flow will ensure a temperature stabilization of the sample, followed by
9) a single scan NMR detection of the polarized sample with arbitrary (multiple pulse) excitation sequence. If the heating is integrated in the NMR detector, one can chose to include a solid phase cross polarization RF pulse sequence to transfer the proton polarization to for example C13 nuclei and detect the carbon NMR signal for additional structural information of the molecules under investigation.
10) the cycle can be repeated by shuttling the liquid sample, along with the capillary back to the DNP polarizer and the sequence continues from step 4). The repetitive sample polarization and NMR analysis allows all known types of multidimensional NMR. In a modification of the above procedure, with an additional NMR coil at the polarizer stage, this includes multidimensional solid state NMR sequences.

Some examples of additional modes of operation are mentioned below:
1) Sequential screening. For intermediate concentration samples and with an estimated enhancement of a factor 100 (30×DNP, 3× Bolzmann) it should be possible to speed up 1D proton experiments with a factor $10^4$, or reduce experiments that would normally take a day of averaging with a less than optimal signal to noise result to a single scan analysis in a time of 10 sec with superior signal to noise. It should be possible to reach enhancements of 500 or more, allowing single scan natural abundance C13 experiments or screening of low concentration metabolites that are beyond the limits of present NMR technology. In particular, the present method may be coupled inline to state of the art chromatography instruments for sample separation and concentration.
2) With an enhancement level of 100 and an additional benefit of an improved sensitivity of a factor 10 by miniaturization, routine analysis becomes possible for much lower sample volumes. For example, cerebral spine fluids is presently studied for sample volumes of about 200 μl. Small animals have only a few micro liters of CSF. In the present setup one can envision a continuous monitoring with samples of only 10 nl taken at various stages of a disease and/or medication treatment without harming the animal, and minimizing the use of animals for testing purposes.
3) Repetitive polarization for structure analysis, hydrogen bonding distances etc. A potential advantage is that solid state correlation experiments can be combined with high resolution liquid state detection and/or liquid state Nuclear Overhauser Effect (NOE) distance measurements. This may provide a way to study conformational changes during the melting of the host solvent. Such 2D/3D experiments are presently prohibitive in measurement time but could be done in typically one hour of experiment.
4) In principle one can choose to work at a single field level. In this case the transport distance can be very short and sequential analysis can be fast. The field should be chosen to match available microwave sources. As an alternative one can use a dual field center magnet, potentially using proprietary ferroshim technology.
5) Resistive high field magnets are very expensive in operational cost. At present it is not possible to change the magnetic field sufficiently fast to do an in-situ multiple field experiment. A quasi-static operation with off-center low field DNP could be a realistic mode of operation that can reduce experimental cost rather substantially.
6) It is possible to perform the NMR detection in the frozen (solid) state. This may allow solid state dual field correlation experiments on various systems with quadrupolar nuclei and may give unique insight in structural details.
7) One can envision a configuration where the NMR detection volume is much smaller than the sample. In this case it is possible to perform a fast 2D experiment in a single DNP enhancement step. This could allow fast identification of molecules that are not resolved in a 1D spectrum.
8) Using liquid He as coolant it is possible to extend the temperature range of the DNP process. This will improve the enhancement at the cost of longer polarization time, but at reduced requirements for the microwave power. This could be beneficial if one aims at higher field/frequencies where high power sources are scarce.

Measurements were performed on heating, cooling and shuttling. These measurements are summarized in below table:

|  | range | verified | expected |
| --- | --- | --- | --- |
| sample shuttling | 35 mm (type) | <50 ms | 20 ms |
| cooling | 300-80 K | <0.5 s (estimated) | <200 ms |
| heating N2 gas 300 K bench test | 80-273 K (Inc. melting) | 1.5 s | <1 sec (80-273) |
| heating N2 gas 300 K bench test | 273-300 K | 1.0 |  |
| heating N2 gas 320 K bench test | 80-300 K | 1.2 s |  |
| rf heating 22 W | 293-350 K | 0.9 |  |
| rf heating 88 W | 293-310 K | 0.1 | 0.1 s (273-300K, including melting) |

With sample shuttling, the length and time is mentioned of the transport between the DNP stage and the NMR stage. As indicated above, the sample may be transported back and forth for the plurality of times, for instance for 3D NMR or other applications. To this end, a quick cooling and heating may also be beneficial. Cooling and heating times, using different heating principles are indicated in the table. Cooling is done by bringing the capillary in contact with liquid or gaseous N2 at N2 boiling temperature. Helium cooling is of course also an option.

The invention claimed is:

1. A rapid cycle dynamic nuclear polarization (DNP) NMR apparatus comprising:
   a cooling unit, configured to cool a sample in a flow-through capillary;
   a DNP polarization unit configured to polarize the sample in the capillary;
   a stripline-based NMR detector comprising a stripline for NMR analysis of the sample in the capillary;
   a transport unit configured to guide the capillary from the DNP polarization unit to the stripline of stripline-based NMR detector; and
   a heating unit configured to heat the sample in the capillary before analysis of the sample by the stripline-based NMR detector.

2. The rapid cycle dynamic nuclear polarization apparatus according to claim 1, further comprising:
   a sample loading unit configured to provide a sample comprising an analyte and a polarizing agent and introduce the sample and DNP radical to the capillary.

3. The rapid cycle dynamic nuclear polarization apparatus according to claim 1, wherein the capillary is configured to contain a plurality of samples, separated by buffers.

4. The rapid cycle dynamic nuclear polarization apparatus according to claim 1, wherein the heating unit comprises a blower for a hot gas.

5. The rapid cycle dynamic nuclear polarization apparatus according to claim 1, wherein the stripline is integrated in a micro chip.

6. The rapid cycle dynamic nuclear polarization apparatus according to claim 1 DNP polarization unit configured to generate microwaves selected from the range of 1-1000 GHz within a microwave resonator, and wherein the stripline-based NMR detector is configured to generate RF pulses with frequencies selected from the range of 5-1000 MHz.

7. The rapid cycle dynamic nuclear polarization apparatus according to claim 1, wherein the transport unit comprises a rotator configured to transport the capillary, a linear translator configured to transport the capillary or a piezo transducer to transport the capillary.

8. A method for DNP-NMR analysis with a stripline-based NMR detector including a stripline for NMR analysis of a sample in a flow-through capillary, the method comprising:
   i. loading the sample comprising an analyte and a polarizing agent in the flow-through capillary, the sample having a volume in the range of 1 nl-20 µl;
   ii. guiding the sample in the capillary to a polarization unit to arrange the sample in the polarization unit, cooling the sample to a temperature below the freezing temperature of the sample, and generating microwaves selected from the range of 1-1000 GHz within the polarization unit to polarize the sample;
   iii. guiding the capillary to the stripline of the stripline-based NMR detector to arrange the sample over a stripline, thawing the sample, applying RF pulses to the sample, and retrieving an NMR signal of the sample in the capillary.

9. The method according to claim 8, wherein the analyte comprises a liquid comprising a metabolite.

10. The method according to claim 8, wherein the analyte comprises a body fluid, such as selected from the group consisting of blood, blood plasma, urine, cerebro spinal fluid.

11. The method according to claim 8, comprising polarizing the sample in a time frame in the range of 1-120 sec, subsequently guiding the capillary to the stripline of the stripline-based NMR detector in a time frame in the range of 20 ms-5 sec, heating the sample, and subsequently retrieving an NMR signal from the sample in a time frame in the range of 1-300 sec.

12. The method according to claim 8, comprising repeating method elements ii and iii.

13. The method according to claim 8, wherein the polarizing agent comprises one or more of a free radical molecule or immobilized radical molecule containing one or more unpaired electron spins or photo-excited triplet spins.

14. The method according to claim 8, including an NMR cross-polarization pulse sequence in the NMR stripline to transfer proton polarization to other low gamma nuclei such as N or C, wherein the sample is still in the frozen state.

15. A method comprising:
   providing a rapid cycle dynamic nuclear polarization NMR apparatus including:
      a cooling unit, configured to cool a sample in a flow-through capillary;
      a DNP polarization unit configured to polarize the sample in the capillary;
      a stripline-based NMR detector comprising a stripline for NMR analysis of the sample in the capillary;
      a transport unit configured to guide the capillary from the DNP polarization unit to the stripline of stripline-based NMR detector; and
      a heating unit configured to heat the sample in the capillary before analysis of the sample by the stripline-based NMR detector,
   using the rapid cycle dynamic nuclear polarization NMR apparatus for multi-dimensional solid state NMR or for metabolic screening or in line quality control.

16. The rapid cycle dynamic nuclear polarization apparatus according to claim 2, wherein the capillary is configured to contain a plurality of samples, separated by buffers.

17. The rapid cycle dynamic nuclear polarization apparatus according to claim 2, wherein the heating unit comprises a blower for a hot gas.

18. The rapid cycle dynamic nuclear polarization apparatus according to claim 3, wherein the heating unit comprises a blower for a hot gas.

19. The rapid cycle dynamic nuclear polarization apparatus according to claim 2, wherein the stripline is integrated in a micro chip.

20. The rapid cycle dynamic nuclear polarization apparatus according to claim 3, wherein the stripline is integrated in a micro chip.

* * * * *